United States Patent
Graf et al.

(10) Patent No.: US 10,267,757 B2
(45) Date of Patent: Apr. 23, 2019

(54) METHOD FOR FABRICATION OF A SENSOR DEVICE

(71) Applicant: Sensirion AG, Stäfa (CH)

(72) Inventors: Silvio Graf, Stäfa (CH); Ulrich Bartsch, Stäfa (CH); Matthias Studer, Stäfa (CH)

(73) Assignee: Sensirion AG, Stäfa (CH)

( * ) Notice: Subject to any disclaimer, the term of this patent is extended or adjusted under 35 U.S.C. 154(b) by 23 days.

(21) Appl. No.: 15/448,140

(22) Filed: Mar. 2, 2017

(65) Prior Publication Data

US 2017/0254769 A1   Sep. 7, 2017

(30) Foreign Application Priority Data

Mar. 3, 2016   (EP) .................................... 16158555

(51) Int. Cl.
*H01L 29/43* (2006.01)
*G01N 27/22* (2006.01)

(52) U.S. Cl.
CPC ........... *G01N 27/225* (2013.01); *H01L 29/43* (2013.01)

(58) Field of Classification Search
None
See application file for complete search history.

(56) References Cited

U.S. PATENT DOCUMENTS

| | | |
|---|---|---|
| 6,679,995 B1 | 1/2004 | Banjac et al. |
| 6,690,569 B1 | 2/2004 | Mayer et al. |
| 6,787,047 B1 | 9/2004 | Hahn et al. |
| 2008/0315332 A1 | 12/2008 | Kaelberer et al. |
| 2014/0175570 A1 | 6/2014 | Lee et al. |
| 2016/0327446 A1 | 11/2016 | Classen et al. |

FOREIGN PATENT DOCUMENTS

| | | |
|---|---|---|
| CN | 1455250 A | 11/2003 |
| WO | WO 01/42776 A1 | 6/2001 |
| WO | WO 01/44822 A1 | 6/2001 |
| WO | WO 2007/068590 A1 | 6/2007 |
| WO | WO 2015/106855 A1 | 7/2015 |

OTHER PUBLICATIONS

Tang, W. et al. "Laterally Driven Polysilicon Resonant Microstructures". Sensors and Actuators, vol. 20, 1989, pp. 25-32.

*Primary Examiner* — Long Pham
(74) *Attorney, Agent, or Firm* — Foley & Lardner LLP

(57) ABSTRACT

A method for fabrication of a sensor device (1) for measuring a parameter of a test substance, comprising: i) providing a substrate; ii) arranging on its front side a structured first protection layer (2); iii) arranging on the substrate with the structured first protection layer (2) a stack including first and second electrodes (3,4), a sacrificial layer between the first and second electrodes (3,4); and iv) etching in an etching step from the back side through the substrate such as to remove material of the semiconductor substrate and the sacrificial layer. The present invention also relates to such a sensor device (1).

23 Claims, 3 Drawing Sheets

METHOD FOR FABRICATION OF A SENSOR DEVICE

TECHNICAL FIELD

The present invention relates to a method for fabrication of a sensor device, the sensor device comprising a sensing structure that includes an electrode arrangement. Moreover, the invention relates to such a sensor device.

PRIOR ART

Sensor devices with electrodes for measuring, for example, humidity of ambient air by applying a capacitive sensing principle are generally known. A humidity sensor device of this kind is described in WO 01/42776. The sensor chip includes an electrode structure that forms a capacitor. During the fabrication process, the sensing structure, i.e. the electrode structure, is typically deposited after etching a sensing cavity into the sensing area. After deposition, the electrode structure is coated with an oxygen barrier material such as to minimize deterioration of the electrodes.

SUMMARY OF THE INVENTION

It is an object of the present invention to provide an improved method for fabrication of a sensor device adapted for measuring a first parameter $P_1$ of a test substance, the first parameter $P_1$ being preferably a humidity of the test substance.

This object is achieved by the method according to claim 1. According thereto, a method for fabrication of a sensor device is proposed, the sensor device being adapted for measuring a first parameter $P_1$ of a test substance. The test substance may be a fluid, in particular a gas such as air. The first parameter $P_1$ may be, for example, a humidity value of the test substance, i.e. an amount of water vapor in ambient air. The method according to invention comprises the steps of:

i) providing a substrate with a front side and a back side, the front and back sides each extending in an in-plane direction and being located at a distance to one another in an out-of-plane direction, the distance being a thickness of the substrate;

ii) depositing from the front side of the substrate a structured first protection layer;

iii) arranging on the front side of the substrate a stack of dielectric and conducting in-plane layers, the stack comprising:
a first electrode;
a second electrode;
a sacrificial layer;
wherein the first and second electrodes are arranged on the first protection layer and at a distance to one another with respect to the in-plane direction,
wherein the sacrificial layer is arranged without overlap with the first protection layer with respect to the in-plane direction and between the first electrode and the second electrode with respect to the in-plane direction;
and the stack further comprising:
a passivation layer that covers front sides of the first and second electrodes and the sacrificial layer, respectively; and iv) generating from the back side of the substrate, in a process step, an opening, the opening extending through the substrate from its back side to its front side and the opening removing at least part of the sacrificial layer, thereby creating a sensing cavity extending between the first electrode and the second electrode, wherein the first protection layer protects the first and second electrodes from being removed during the process step iv).

In the context of the present invention, the term "sacrificial layer is arranged without overlap with the first protection layer with respect to the in-plane direction" means that the sacrificial layer is not arranged on the first protection layer. In other words: The sacrificial layer is located at a distance or directly adjacent to the first protection layer with respect to the in-plane direction.

During the process step iv) according to invention, an opening is manufactured into the substrate, from the substrate's back side. By means of the process step iv) the opening is created as a through opening extending from the back side to the front side of the substrate and deeper, such that the sacrificial layer that is located on the substrate's front side is removed at least in part, preferably entirely. The opening extents therefore into a space that separates the first and second electrodes in in-plane direction. Accordingly, the opening defines a sensing cavity extending between the first and second electrodes, where a dielectric may be located. The opening may have, in the substrate, an in-plane width or diameter ranging, for example, from 100 micrometers to 2000 micrometers, preferably 100 micrometers to 1000 micrometers.

In some embodiments, the process step iv) may be a single etching step, preferably a deep reactive-ion etching process step.

In some other embodiments, the process step iv) may have multiple steps including several etching steps. A first etching step may be a KOH wet-etching step, a consecutive etching step may include a $SF_6$ plasma etching step. Also, the deep reactive-ion etching process may be performed in a first step with a first set of parameters, and, afterwards, in a second step with a second set of parameters, the first and second set of parameter differing in at least one parameter. In some embodiments, further steps with predefined sets of parameters may be applied.

In some embodiments, the first and second electrodes then may be used as plates of a capacitor while the sensing principle is to measure by means of the electrodes a change of said dielectric, more precisely a change of the dielectric property such as the relative permittivity, when the dielectric is in contact with the test substance or is the test substance itself.

The present invention is based on the insight that the sensing structure, i.e. the first and second electrodes and the sensing cavity extending therebetween, may be revealed from the source material simultaneously with introducing the opening into the substrate. Accordingly, in the process step iv), the opening is formed into the substrate from its back side, the sensing electrode structure is revealed, and the sensing cavity is created by removing at least part of the sacrificial layer that is originally arranged between the first and second electrodes. Arranging the sacrificial layer between the first and second electrodes therefore allows creating the sensing cavity in the process step iv) and as required by the sensor architecture simpler and faster.

In some embodiments, the process step iv) is a deep reactive-ion etching process step. The structured first protection layer acts as an etching stop and prevents etching of the first and second electrodes during the process step iv). As the first protection layer is, however, exposed to the etching procedure, it may be thinned out. The sacrificial layer is, as described above, not protected by the first protection layer and exposed to the etching process step and at least partly, preferably completely, etched away.

The sensor device may, in some embodiments, be a humidity sensor. In the context of the present invention, the term "humidity" is to be understood as the quantity of water vapor or another fluid contained in the test substance, the test substance may be, for example ambient air, containing the vapor. Depending on the specific application, the relative or the absolute humidity may be evaluated based on the sensor response.

In some embodiments, the sensing cavity may be partly or completely filled with a sensitive substance. It is to be understood that the sensing cavity may extend over a part of or over the entire extent of the opening. The sensitive substance may be chosen such that it has a second parameter $P_2$, wherein the second parameter $P_2$—or its variation—is measurable by means of the electrode structure. In these embodiments, the measurement principle includes bringing the test substance into contact with the sensitive substance, wherein the sensitive substance and its second parameter $P_2$ are chosen such that the second parameter $P_2$ varies upon variation of the first measurement parameter $P_1$ of the test substance.

The first and second electrodes may thus, in some embodiments, form a capacitor with the sensitive substance acting as a dielectric in the capacitor.

In some embodiments, the sensitive substance may be a polymer substance and the second parameter $P_2$ may be a relative permittivity $\in_r$ of that polymer substance. The polymer substance may be chosen such that its relative permittivity $\in_r$ changes upon absorption or desorption of humidity from the test substance when the polymer substance is in contact with the test substance. This may further increase a sensitivity of the sensor device.

In some embodiments, the first and second electrodes are structured in an interdigitated manner with respect to one another, i.e. electrode fingers interdigitate into one another. This may further increase sensitivity of the sensing structure.

In some embodiments, the sensitive substance layer may have an out-of-plane thickness of the sensitive substance of 0.5 micrometers to 15 micrometers, preferably 5.6 micrometers to 8.4 micrometers, in particular 7 micrometers.

In some embodiments the sensitive substance may be deposited through the opening directly onto the sensing structure exposed during the process step iv) according to invention, or it may be deposited on a third protecting layer (see below), the third protecting layer covering the sensing structure. The sensitive substance may be deposited by means of contact-less dispensing such as printing, spray coating, and/or contact-less micro-dispensing.

In some embodiments, the substrate may be made from a semiconductor material, preferably from silicon. It is advantageous if the substrate is part of a silicon wafer, wherein this silicon wafer may be a standard wafer as used in standard CMOS technology. An out-of-plane thickness of the substrate may be 100 nanometers to 1000 nanometers, in particular 200 nanometers to 500 nanometers. This may simplify the fabrication of the sensor device. In some other embodiments, the substrate may comprise or consist of ceramic, glass, polymer, or other dielectric materials.

In some embodiments, the first and second electrodes and the sacrificial layer may be made from standard CMOS polysilicon layer materials. Here, the first and second electrode as well as the sacrificial layer may each be made from a different material or material combination. Alternatively, two or all elements chosen from the group comprising the first and second electrodes and the sacrificial layer are made from the same material or material combination. Accordingly, the first and second electrodes and the sacrificial layer may be integrated into the stack, the stack being from standard CMOS layers. It is particularly preferred to make the first and second electrodes as well as the sacrificial layer from doped polysilicon.

The first and second electrodes may each have an out-of-plane thickness of 50 nanometers to 250 nanometers, preferably of 160 nanometers to 240 nanometers, more preferably of 200 nanometers. Typical in-plane widths of the first and second electrodes may be 80 nanometers to 1000 nanometers, preferably of 140 nanometers to 260 nanometers or may be 200 nanometers.

The sacrificial layer may have an out-of-plane thickness of 50 nanometers to 250 nanometers, preferably of 160 nanometers to 240 nanometers, more preferably of 200 nanometers and an in-plane width of 80 nanometers to 1000 nanometers, preferably of 140 nanometers to 260 nanometers, more preferably of 200 nanometers.

In some embodiments, an in-plane distance between the first electrode or second electrode and the sacrificial layer may be at least 150 nanometers, preferably 220 nanometers to 340 nanometers, more preferably 280 nanometers.

In some embodiments, an in-plane distance between the first electrode and the second electrode may be 150 nanometers to 1000 nanometers, preferably 400 nanometers to 600 nanometers, more preferably 500 nanometers.

In some embodiments, the passivation layer may cover the entire measurement field or more of the sensor device. The passivation layer may have an out-of-plane thickness of 500 nanometers to 1500 nanometers, preferably 720 nanometers to 1080 nanometers, more preferably of 900 nanometers. In some embodiments, the passivation layer may comprise or consist of $SiO_2$.

In some preferred embodiments, the structured first protection layer may be a layer used as used in standard CMOS technology, preferably a silicon oxide or silicon nitride layer. An out-of-plane thickness of the structured first protection layer ranges from 100 nanometers to 600 nanometers.

In some embodiments, the process step iv) thins the first protection layer out by a certain amount, for example, by 80 nanometers to 150 nanometers. It is preferred, that material and initial thickness of the first protection layer, i.e. before the process step iv) according to invention is applied, is chosen such that, after the process step iv) according to invention has been carried out, the out-of-plane thickness of the first protection layer is about 100 nanometers to 600 nanometers, more preferably 320 nanometers to 480 nanometers, even more preferably 400 nanometers. In this case, a part of the out-of-plan thickness of the first protection layer is sacrificed during the process step for protection for the first and second electrodes 3, 4.

In some preferred embodiments, the first protection layer and the first and second electrodes are designed such that paths of the structured first protection layer protrude in in-plane direction over the respective first or second electrode by at least 100 nanometers on either side in the in-plane direction. In other words: The paths for the first protection layer are wider than the electrodes. Thereby, it is ensured that the entire first and second electrode is protected by the first protection layer during the process step iv).

In some embodiments, the first protection layer is removed after the process step iv). In a further step, a sensitive structure including the first and second electrodes is created, wherein the sensitive structure allows using resistivity measurements as the sensing principle. One then measures a resistivity of the material in the sensing cavity. Therefore, the sensing cavity may be at least partly or completely filled with a sensitive substance, wherein the sensitive substance has a resistivity that varies with variation of the first parameter $P_1$ of the test substance. In this case, the resistivity determined by means of the electrodes is used as a measure for the first parameter $P_1$ of the test substance.

In some embodiments, a further protection layer, a second protection layer, is used to properly deposit and to protect the electrode and sacrificial layer structure. The second protection layer covers the first and second electrodes, preferably also the sacrificial layer, and is arranged between the passivation layer and the first and second electrode and the sacrificial layer, respectively. The second protection layer is part of the stack and preferably applied before the deposition of the passivation layer. The second protection layer is designed to protect the first and second electrodes, in particular after completion of the sensor device, against external influences such as, for example, oxidation. The second protection layer is preferably arranged to shield the first and second electrodes against external influences such as, for example, oxygen from the passivation layer. The second protection layer may have an out-of-plane thickness of 30 nanometers to 250 nanometers, preferably 80 nanometers to 120 nanometers, more preferably of 100 nanometers and may comprise or consist of SiN or other suitable materials.

Preferably, the process step iv) is designed such that the first and second electrodes remain covered by the second protection layer, i.e. the second protection layer sections that are in direct contact with the first and second electrodes are not removed during the process step iv). In these embodiments, the first and second electrodes are covered on the lateral and the front side by the second protection layer.

In some embodiments, after the process step iv), i.e. after the opening has been created, the exposed back side of the stack, i.e. the first protection layer—or the back sides of the electrodes, if the first protection layer has been removed—, is covered by a third protection layer. The third protection layer may have an out-of-plane thickness of 30 nanometers to 350 nanometers, preferably of 120 nanometers to 180 nanometers, more preferably of 150 nanometers, and may be made from SiN or other suitable materials.

In some embodiments of the method according to invention, a plurality of sensor chips may be manufactured from a single wafer. The wafer may be diced after completion of the manufacturing process of the single sensor chips, or, in the alternative, the wafer may be diced, whereupon the sensor chips are completed.

It is another object of the present invention to provide a sensor device that may be more efficiently produced.

This object is achieved by the sensor device according to claim 11. According thereto, a sensor device for measuring a first parameter $P_1$ of a test substance, the first parameter $P_1$ being preferably a humidity of the test substance, is proposed. The sensor device comprises:

a substrate, preferably a silicon substrate, having a first side and a second side, the first and second sides each extending in an in-plane direction and being located at a distance to one another in an out-of-plane direction and the first side being preferably a front side and the second side being preferably a back side of the substrate, the substrate having an opening extending from the second side to the front side of the substrate;

a stack arranged on the first side of the substrate and at least partly, preferably completely, spanning the opening;

a first electrode and a second electrode arranged in the stack such as to overlap with the opening with respect to the in-plane direction, the first electrode and the second electrode being separated in the in-plane direction by a space from one another;

wherein the opening is further extending at least partly into the space between the first electrode and the second electrode, thereby delimiting a sensing cavity extending therebetween;

wherein the space is delimited in out-of-plane direction by an end surface that extends in in-plane direction, and wherein the end surface is free of an etch stop structure.

In some preferred embodiments, a structured first protection layer is arranged on second sides, preferably the back sides, of the first and second electrodes, the structured first protection layer as outlined above. The first protection layer is adapted to protect the first and second electrodes from being damaged during the etching process that forms the opening and the sensing cavity, and, preferably, it is a layer as used in standard CMOS technology, preferably a silicon oxide or a silicon nitride layer.

In some embodiments, the substrate of the sensor is made from a semiconductor material, preferably from silicon as outlined above. In some embodiments, the first protection layer has an out-of-plane thickness from 100 nanometers to 600 nanometers, more preferably from 320 nanometers to 480 nanometers, even more preferably is 400 nanometers.

In some embodiments, the structured first protection layer protrudes in in-plane direction over the first and second electrodes by up to 50 nanometers or more, preferably by up to 100 nanometers or more, i.e. the structured first protection layer paths are wider in in-plane direction than the electrodes. In other embodiments, the structured first protection layer is removed after the process step iv), accordingly, there is no such protrusions.

In some embodiments, the first and second electrodes are made from standard CMOS polysilicon layer materials, preferably from doped polysilicon.

Preferably, the opening is at least partially, preferably completely, filled with a sensitive substance, the sensitive substance being chosen such that it has a measurable second parameter $P_2$, wherein, when the sensitive substance is in contact with the test substance, the second parameter $P_2$ of the sensitive substance varies upon variation of the first measurement parameter $P_1$ of the test substance. The second parameter $P_2$ may be a permittivity or a resistivity parameter as explained above. The sensing structure may, however, be designed to measure other second (or first) parameters by implementing known sensing principles.

An aspect the present invention relates to a sensor chip with a sensor device according to the invention, wherein the sensor chip comprises integrated circuitry as herein described, and a computer program product that comprises a computer program code. The computer program code, when carried out in the integrated circuitry, may cause the sensor device to measure at least one first parameter $P_1$ of the test substance, preferably by measuring the second parameter $P_2$ of the sensitive substance, if any.

The computer program code may be provided in a source code, in a machine-executable code, or in any intermediate form of code-like object code. It can be provided as a computer program product on a computer-readable medium in tangible form, e.g. on a CD-ROM or on a Flash ROM memory element, or it can be made available in the form of a network-accessible medium for download from one or more remote servers through a network.

An area of the sensor device may be 100 micrometers by 100 micrometers.

The sensor chip may be equipped with additional packaging such as at least one further sensor device, a housing, or the like and may be mounted onto a circuit board.

It is to be understood that the sensor device may be designed as a gas sensor, for example, a humidity sensor, a fluid flow sensor, a pressure sensor, or another sensor device using the sensing structure of similar architecture.

In a further aspect, the present invention relates to the use of the sensor device according to invention or the herein described sensor chip with the sensor device according to invention in such a way that the test substance is brought into contact with the sensing cavity of the sensor device or with the sensitive substance, if any, wherein the sensor device is then operated to measure the at least one first parameter $P_1$ of the test substance directly or indirectly through the sensitive substance.

It is to be understood that these embodiments and aspects will be better understood when considered with the description of the preferred embodiments below. Aspects may be combined with one another without departing from the scope of the appended claims and further embodiments may be formed with parts or all the features of the embodiments as described herein.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Preferred embodiments of the present invention are described with reference to FIGS. 1 to 6.

Figure 1:
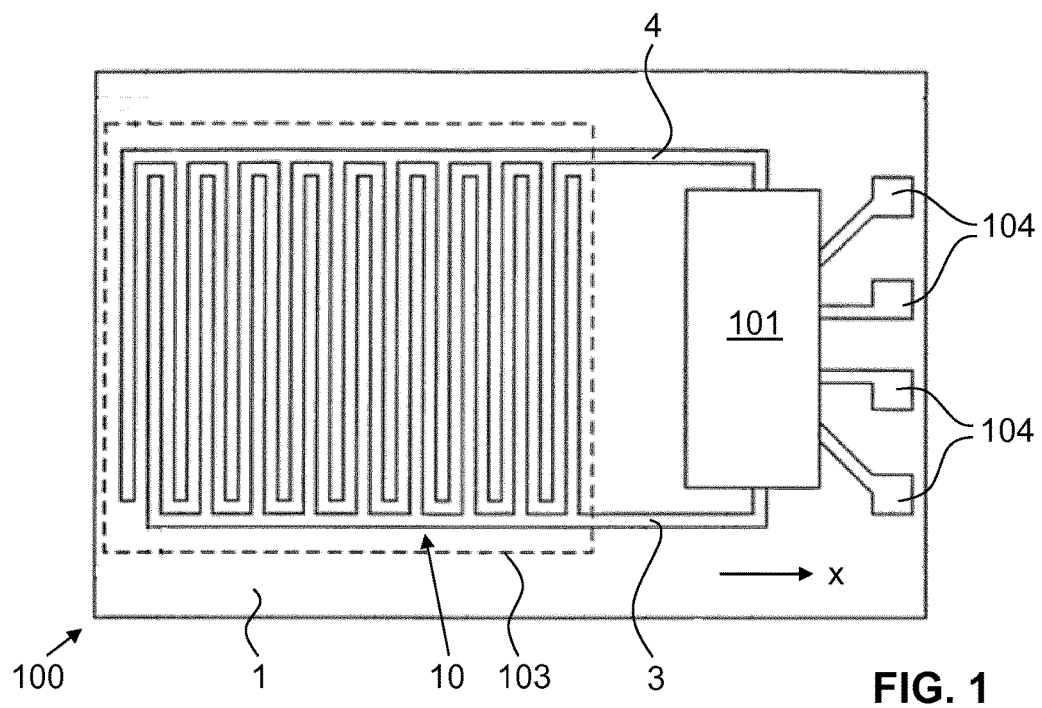
FIG. 1 shows, in a top view, an embodiment of a sensor chip with a sensor device on a semiconductor substrate, the sensor device comprising a first and a second electrode, the first and second electrodes being arranged in an interdigitated manner and forming the sensitive structure of the sensor device.

FIG. 1 shows, in a top view, an embodiment of a sensor chip 100 with a sensor device 1 on a substrate 10. The sensor device 1 is designed for measuring, as a first parameter $P_1$, a humidity value of a test substance. The test substance may be ambient air. The sensor device 1 has a first electrode 3 and a second electrode 4, the first and second electrodes 3, 4 being arranged in an interdigitated manner with respect to one another and spanning a measurement field 103 of the sensor device 1. The measurement field 103 may have an area of about 100 micrometers by 100 micrometers.

Figure 4:
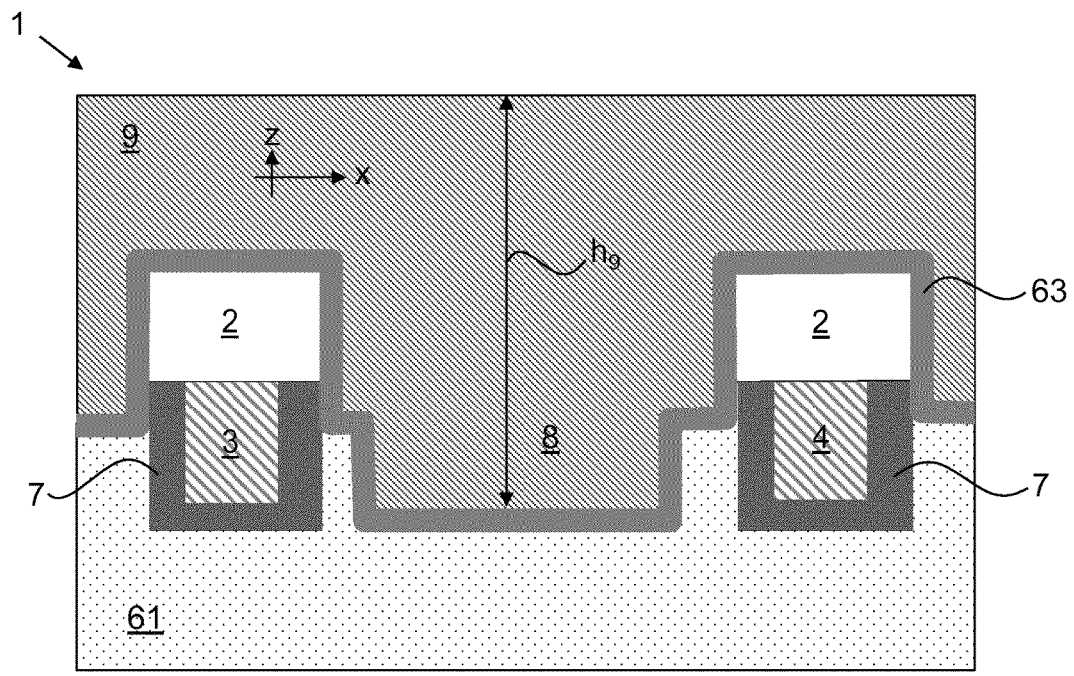
FIG. 4 shows the layer arrangement according to FIG. 3 after a sensitive substance has been deposited to cover the sensing structure.

The measurement field 103 is covered by a sensitive substance 9 (cf. FIG. 4). The sensitive substance 9 may be a polymeric or a ceramic material, wherein the sensitive substance 9 has a second parameter $P_2$, wherein said second parameter $P_2$ may be measured by means of the sensor device 1 and wherein, when the sensitive substance 9 is in contact with the test substance, the second parameter $P_2$ of the sensitive substance 9 varies upon variation of the measurement parameter $P_1$ of the test substance due to, for example, a change in the external conditions. Polymeric material of the sensitive substance 9 may absorb or desorption humidity, i.e. water vapor in the air, which changes the relative permittivity of the sensitive substance 9. As the sensitive substance 9 acts as a dielectric of the capacitor formed by the first and second electrodes 3, 4, said changing relative permittivity may be accessed by measuring the properties of said capacitor.

An active integrated circuitry 101 is integrated into the sensor chip 100. The integrated circuitry 101 may comprise, for example, evaluation and/or amplification circuitry for reading out a signal, such as a change in the relative permittivity of dielectric of the capacitor, picked-up by the sensing structure formed by the first and second electrodes 3, 4. Preferably, the integrated circuitry 101 is located outside the measurement field 103. A connecting structure 104 provides electric outside-world connection to the sensor chip 100 for the purpose of data transfer and/or power supply.

The integrated circuitry 101 may comprise a computer program product comprising a processor unit (CPU, µP), a non-volatile (e.g. a flash ROM) memory, and a volatile (RAM) memory. The processor communicates with the memory modules. The non-volatile memory stores, inter alia, received or generated signals, as well as a machine-executable program code for execution in the processor. Via a data interface, the processor may communicate with various peripherals, including, for example and depending on the application, the sensor device 1 and a user interface. The user interface may include, e.g., at least one of a network interface for interfacing with an external input/output device, a dedicated input device such as a keyboard and/or mouse for inputting, e.g., a measurement scheme or the like, and a dedicated output device, such as, e.g., an LCD screen for displaying information.

Figure 2:
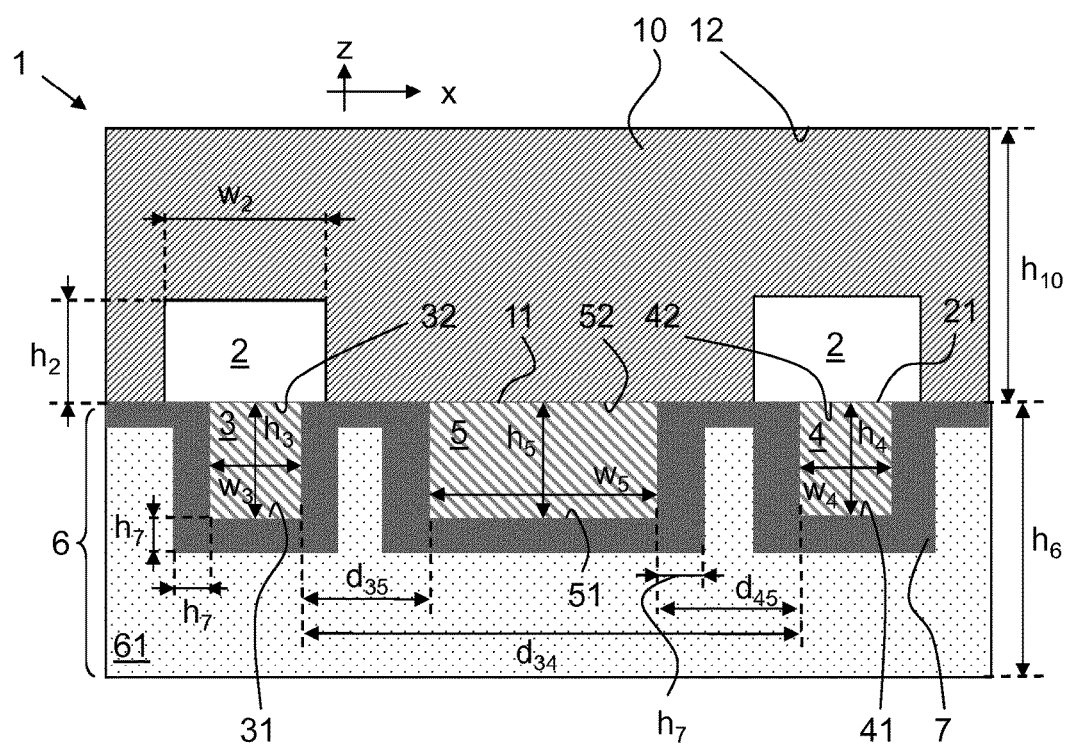
FIG. 2 shows, in a cross-sectional view, an embodiment of the pre-processed sensor device before a measurement opening is etched in a process step iv) according to invention through the semiconductor substrate and into a stack of dielectric and conducting layers arranged on the semiconductor substrate.

FIG. 2 shows, in a cross-sectional view, an embodiment of the sensor device 1 before an opening 13 (cf. FIG. 3) is etched in a process step iv) according to invention into the structure.

In a first step of an embodiment of the method according to invention, the substrate 10 is provided. The substrate 10 is a semiconductor substrate, preferably made from silicon; it may be part of a standard silicon wafer as commonly used in standard CMOS technology. The substrate 10 extends along and in-plane direction x and may have an out-of-plane thickness $h_{10}$ extending along an out-of-plane direction z. In FIG. 1, the out-of-plane direction z points out of the drawing sheet. The out-of-plane thickness $h_{10}$ ranges from 100 micrometers to 1000 micrometers, in particular 200 micrometers to 500 micrometers.

The substrate 10 has a front side 11 and a back side 12. On or in the substrate 10 there is provided a first protection layer 2 that is structured to outline a path of the first and second electrodes 3, 4, i.e. the first protection layer 2 is arranged in a meander pattern on the substrate 10.

If the first protection layer 2 is provided in the substrate 10, it is provided preferably such that front sides 11 and 21 of the substrate and the first protection layer 2, respectively, are flush with one another.

The first protection layer 2 may be a silicon oxide or a silicon nitride layer. Moreover, the first protection layer 2 protects the first and second electrodes 3, 4 during the process step iv) according to invention.

As for the structure of the first protection layer 2: The first protection layer 2 has an out-of-plane thickness $h_2$ of 100 nanometers to 600 nanometers. It is preferred that $h_2$ has a value that, after the process step iv) according to invention (see below), is 100 nanometers to 600 nanometers, more preferably 320 nanometers to 480 nanometers, even more preferably is 400 nanometers. An initial out-of-plane thickness $h_2$ may be 380 nanometers to 580 nanometers, preferably 480 nanometers. A width $w_2$ the first protection layer 2 is chosen such that, in the final sensor device 1, the first protection layer 2 sections, i.e. its paths, protrude in in-plane direction over the respective first or second electrodes 3, 4 by 100 nanometers to either side in in-plane direction x, i.e. the width $w_2$ of the paths of the first protection layer 2 is 200 nanometers wider than the width of the first and second electrodes 3, 4 in in-plane direction x. An in-plane width $w_2$ of the first protection layer 2 may be 80 nanometers to 1000 nanometers, preferably 140 nanometers to 260 nanometers, more preferably 200 nanometers.

After providing the substrate 10, a stack 6 of dielectric and conducting layers as commonly used in CMOS technology is deposited onto the front side 11 of the substrate 10 with the structured first protection layer 2. The dielectric and conducting layers of the stack 6 extend along the in-plane direction x. The stack 6 comprises the first electrode 3 and the second electrode 4, as well as a sacrificial layer 5. Moreover, the stack 6 comprises a second protection layer 7 and a passivation layer 61.

In some other embodiments, further elements may be comprised in the stack 6 depending on the specific application of the sensor device 1.

The first and second electrodes 3, 4 are arranged on the structured first protection layer 2 and at the distance to one another in the in-plane direction x to form an interdigitated electrode structure which constitutes a structured capacitor. The sections of the first protection layer 2 (i.e. its paths) that carry the first electrode 3 are located at the distance of the first protection layer 2 that carry the second electrode 4; accordingly, the structured first protection layer 2 mirrors that interdigitated pattern of the electrode structure.

The sacrificial layer 5 is arranged between the first and second electrodes 3, 4 with respect to the in-plane direction x. Moreover, the sacrificial layer 5 is arranged outside the first protection layer 2, i.e. it does not overlap with the first protection layer 2 in in-plane direction x.

Out-of-plane heights $h_3$, $h_4$, $h_5$ of the first and second electrodes 3, 4 and the sacrificial layer 5, respectively, are 50 nanometers to 250 nanometers, preferably 160 nanometers to 240 nanometers, more preferably 200 nanometers each. In-plane widths $w_3$, $w_4$, $w_5$ of the first and second electrodes 3, 4 and the sacrificial layer 5, respectively, may be 80 nanometers to 1000 nanometers, preferably 140 nanometers to 260 nanometers, in particular 200 nanometers.

In-plane distances $d_{35}$, $d_{45}$ between the first or second electrodes 3, 4 and the sacrificial layer 5, respectively, may be at least 150 nanometers, preferably 220 nanometers to 340 nanometers, more preferably 280 nanometers.

An in-plane distance $d_{34}$ between the first electrode 3 and the second electrode 4 may be 150 nanometers to 1000 nanometers, preferably 400 nanometers to 600 nanometers, more preferably 500 nanometers.

The first and second electrodes 3, 4 and the sacrificial layer 5 may be made from standard CMOS polysilicon layer materials, preferably from doped polysilicon.

The stack 6 is grown such that the first and second electrodes 3, 4 and the sacrificial layer 5 are coated, on their front sides 31, 41, 51, with the second protection layer 7, the second protection layer 7 being a barrier against external influences, such as oxygen, in order to protect the first and second electrodes 3, 4 from deteriorating during use of the sensor device 1. Preferably, the second protection layer 7 is a highly oxygen proof barrier material such as SiN. A thickness $h_7$ may be 30 nanometers to 250 nanometers, preferably 80 nanometers to 120 nanometers, more preferably 100 nanometers. The lateral sections of the protection layer 7 extending in the out-of-plane direction z may act as spacers between the sacrificial layer 5 and the first or the second electrodes 3, 4, respectively.

The passivation layer 61 may cover the entire measurement field 103, in particular the first and second electrodes 3, 4 and the sacrificial layer 5. The passivation layer 61 may have an average out-of-plane thickness $h_{61}$ of 500 nanometers to 1500 nanometers, preferably 720 nanometers to 1080 nanometers, more preferably of 900 nanometers. Preferably, the passivation layer 61 comprises or consists of $SiO_2$.

After providing the substrate 10 with the stack 6, in a next step, the opening 13 (cf. FIG. 3) is etched from the back side 12 of substrate 10 into the substrate 10 in during the process step iv), the process being, for example, a deep reactive-ion etching process step, a SF6 plasma etching step, a KOH wet-etching step, or any combination thereof.

Figure 3:
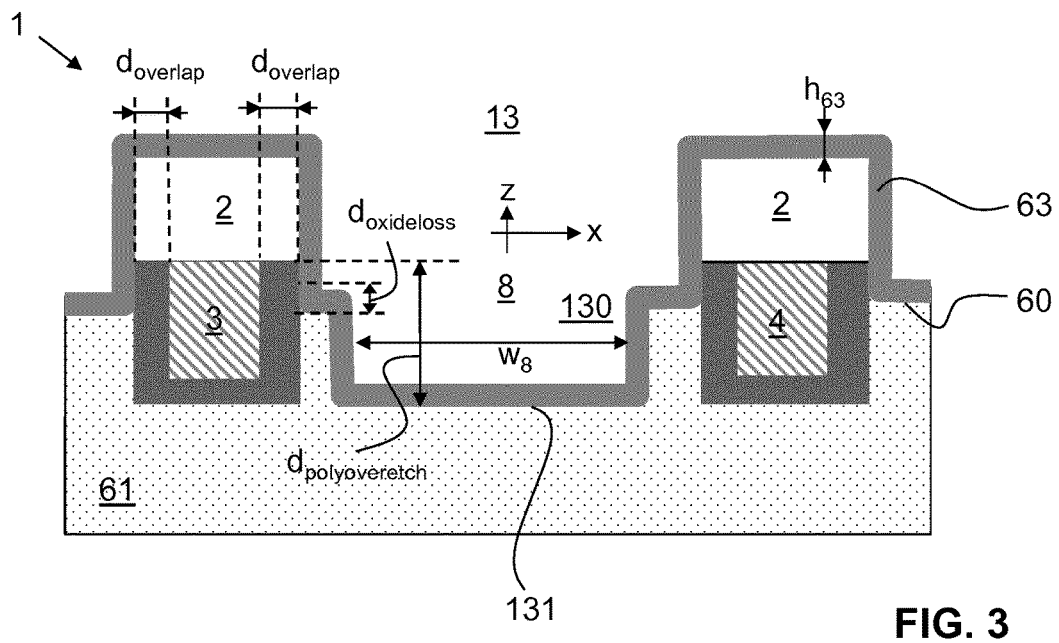
FIG. 3 shows, in a cross-sectional view, the layer arrangement according to FIG. 2 after the process step iv) has been carried out.

FIG. 3 shows the result of this process step iv) according to invention. The process step iv) according to invention is designed such that the final opening 13 extends from the back side 12 to the front side 11 and further into the stack 6 of the sensor device 1. Moreover, the sacrificial layer 5 has been removed by the same process step iv) thereby creating a sensing cavity extending between the first and second electrodes 3, 4.

In the present embodiment, the sacrificial layer 5 has been completely removed but in other embodiments only part of the sacrificial layer 5 is removed.

As the first protection layer 2 is exposed to the etching action during the process step iv), it has been reduced in thickness from an initial thickness of 480 nanometers to a final thickness of 400 nanometers. Sections of the second protection layer 7 that are arranged without overlap in the in-plane direction x with the first protection layer 2 are completely or partially removed by the process step iv); accordingly, only sections of the second protection layer 7 that are in direct contact with the first and second electrodes 3, 4—and therefore enjoy protection by the electrode overlapping first protection layer 2 from being removed by the etching step—remain on the sensor device 1. In this context it is noted again that the first protection layer 2 extends over a distance $d_{overlap}$ beyond the first and second electrodes 3, 4 to either side in in-plane direction x by more than 100 nanometers (cf. FIG. 3). Thereby it is insured that sections of the second protection layer 7, which are protecting the first and second electrodes 3, 4 from deteriorating, are not removed during the process step iv). Accordingly, the first and second electrodes 3, 4 are enclosed by the first and second protection layers 2, 7 (cf. FIG. 3).

As a result of the process step iv), a part of the passivation layer 61 has been removed as well. An extent $d_{oxideloss}$ in out-of-plane direction z of this material loss may be on the 20 nanometers to several hundred nanometers.

Due to the removal of the sacrificial layer 5, the opening 13 extends into a space 130 between the first and second electrodes 3, 4 in in-plane direction x. Accordingly, the sensing cavity 8 extends between the first and second electrodes 3, 4. A total out-of-plane depth $d_{polyoveretch}$, located at the position where the sacrificial layer 5 had been and as measured from the back side 32, 42 of the first and second electrodes 3, 4 to an in-plane end surface 131 of the space 130, may be 200 nanometers to 700 nanometers, preferably 340 nanometers to 500 nanometers, more preferably of 420 nanometers. The total out-of-plane depth $d_{polyoveretch}$ may, in some embodiments, be calculated as $h_5+h_7+d_{oxidloss}$, i.e. during the process step iv), the sacrificial layer is removed (giving an initial depth of $h_5$), the second protection layer 7 is removed (adding another $h_7$ to the total depth $d_{polyoveretch}$), and, some of the passivation layer 61 is lost due to over etching (adding another $d_{oxidloss}$ of about 120 nanometers to 200 nanometers to the total depth $d_{polyoveretch}$).

After the opening 13 is processed into the sensor device 1, a third protection layer 63 may be deposited onto the revealed sensing structure, i.e. over the structured first protection layer 2 and onto the structured back side 60 of the stack 6 as shown in FIG. 3. The third protection layer 63 may be a SiN layer that is deposited with a thickness of $h_{63}$ of 20 nanometers to 350 nanometers, preferably of 120 nanometers to 180 nanometers, more preferably 150 nanometers. The third protection layer 63 protects the revealed structure from damage and/or deterioration.

As a result, a sensing cavity 8 has been created, during the process step iv), extending in in-plane direction x between the first and second electrodes 3, 4. A width $w_8$ of the sensing cavity 8 between the first and second electrodes 3, 4 may be 400 nanometers.

In the next step, at least the sensing cavity 8, preferably the entire opening 13, may be partially or completely filled with a sensitive substance 9 (cf. FIG. 4). The sensitive substance 9 is deposited into opening 13 preferably by means of micro-dispensing or ink-jetting. The sensitive substance 9 may be a polymeric material that absorbs or desorption water vapor from the test substance upon contact between the sensitive substance and the test substance. An out-of-plane thickness $h_9$ of the sensitive substance may be 0.5 micrometers to 15 micrometers, preferably 5.6 micrometers to 8.4 micrometers, in particular 7 micrometers.

FIG. 4 shows a sensor device 1 after completion.

Figure 5:
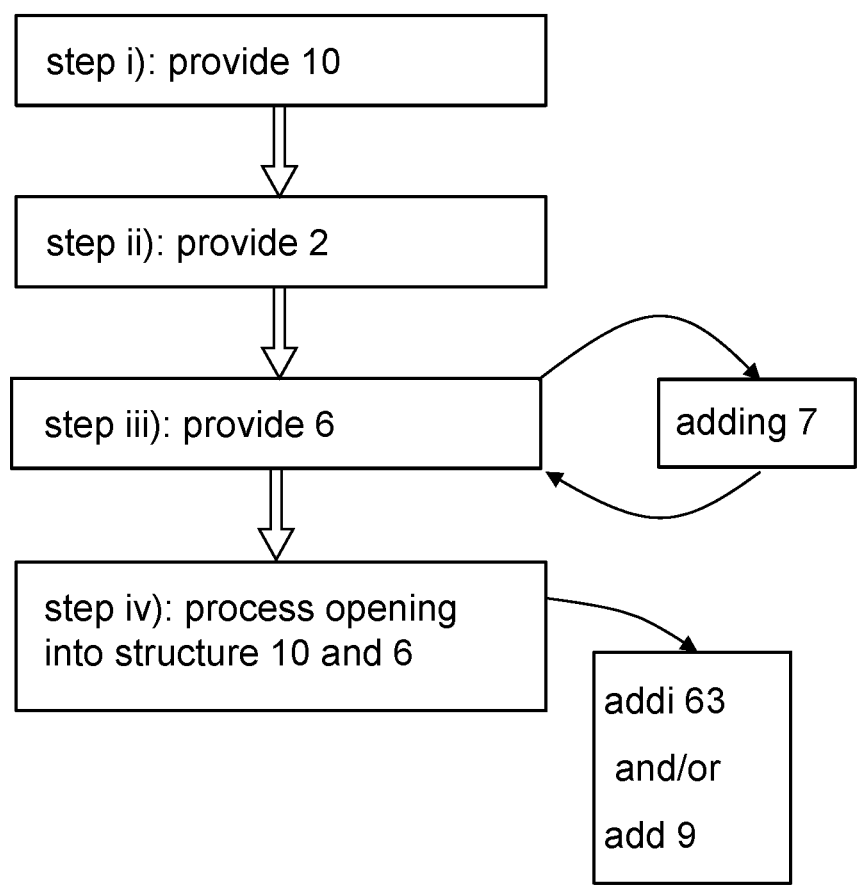
FIG. 5 shows a block diagram of an embodiment of the method according to the present invention.

FIG. 5 shows in a simplified block diagram that method according to invention in a preferred embodiment. In step i), the substrate 10 is provided, thereafter, in step ii), the structured first protection layer 2 is deposited onto the front side 11 of the substrate 10. In step iii), the stack 6 is deposited on the front side 11 of the substrate 10 with the structured protection layer 2. Optionally, the second protection layer 7 is included in stack 6. In the process step iv) the opening 13 is processed into the substrate 10 and the stack 6. In preferred embodiments, the third protection layer 63 is deposited onto the revealed sending structure including the first and second electrodes 3, 4 and/or the sensitive substance 9 is filled into at least part of the opening 13.

It is to be understood that different designs of the sensor device 1 may be created depending on the requirements of the specific application. The present invention is particularly advantageous as the opening 13, which extends as a through hole through the entire substrate 10 and into stack 6 such as to remove at least part of the sacrificial layer 5, is processed into the sensor device 1 in the process step iv), the process step iv) being a single or a plurality of deep reactive-ion etching process steps and/or a KOH wet-etching step and/or a $SF_6$ plasma step or any combination thereof. This simplifies the manufacturing process of such sensor devices. Also, the entire manufacturing process may be designed with standard CMOS materials and standard CMOS process steps. In particular, the electrode structure comprising the first and second electrodes 3, 4, as well as the sacrificial layer 5, may be made from poly silicon available in the standard CMOS process.

| LIST OF REFERENCE SIGNS | |
|---|---|
| 1 | sensor device |
| 10 | substrate of 1 |
| 11 | first or front side of 10 |
| 12 | second or back side of 10 |
| 13 | opening |
| 130 | space |
| 131 | end surface of 130 |
| 100 | sensor chip with 1 |
| 101 | integrated circuitry of 100 |
| 103 | measurement field of 1 |
| 104 | connecting structure |
| 2 | first protection layer |
| 21 | front side of 2 |
| 3 | first electrode |
| 31 | front side of 3 |
| 32 | back side of 3 |
| 4 | second electrode |
| 41 | front side of 4 |
| 42 | back side of 4 |
| 5 | sacrificial layer |
| 51 | front side of 5 |
| 52 | back side of 5 |
| 6 | stack |
| 60 | back side of 6 |
| 61 | passivation layer |
| 63 | third protection layer |
| 7 | second protection layer |
| 8 | sensing cavity |
| 9 | sensitive substance |
| $d_{34}$ | in-plane distance between 3 and 4 |
| $d_{35}$ | in-plane distance between 3 and 5 |
| $d_{45}$ | in-plane distance between 4 and 5 |
| $d_{overlap}$ | part of 2 that extends beyond the electrode in x |
| $d_{oxideloss}$ | extent of loss of 61 |
| $d_{polyoveretch}$ | depth of space 130 in z |
| $P_1$ | first parameter of a test substance |
| $P_2$ | second parameter of sensing substance |
| $h_2$ | out-of-plane thickness of 2 |
| $h_3$ | out-of-plane thickness of 3 |
| $h_4$ | out-of-plane thickness of 4 |
| $h_5$ | out-of-plane thickness of 5 |
| $h_7$ | thickness of 7 |
| $h_9$ | out-of-plane thickness of 9 |
| $h_{10}$ | out-of-plane thickness of 10 |
| $h_{61}$ | out-of-plane thickness of 61 |
| $h_{63}$ | out-of-plane thickness of 63 |
| $w_2$ | in-plane width of 2 |
| $w_3$ | in-plane width of 3 |
| $w_4$ | in-plane width of 4 |
| $w_5$ | in-plane width of 5 |
| $w_8$ | in-plane width of 8 |
| x | in-plane direction |
| z | out-of-plane direction |

The invention claimed is:

1. A method for fabrication of a sensor device, the sensor device being configured to measure a first parameter of a test substance, the method comprising the steps of:

i) providing a substrate with a front side and a back side, the front and back sides each extending in an in-plane direction and being located at a distance to one another in an out-of-plane direction;
ii) depositing a structured first protection layer on or in the front side of the substrate;
iii) arranging a stack of dielectric and conducting in-plane layers on the front side of the substrate, the stack comprising:
   a first electrode;
   a second electrode;
   a sacrificial layer; and
   a passivation layer that covers front sides of the first and second electrodes and the sacrificial layer, respectively;
wherein the first and second electrodes are arranged on the first protection layer and at a distance to one another in the in-plane direction,
wherein the sacrificial layer is arranged without overlap with the first protection layer with respect to the in-plane direction and between the first electrode and the second electrode with respect to the in-plane direction;
wherein the method further comprises:
iv) generating, in a process step, an opening from the back side of the substrate, the opening extending through the substrate from the back side to the front side, and the opening removing at least part of the sacrificial layer, thereby creating a sensing cavity extending between the first electrode and the second electrode, wherein the first protection layer protects the first and second electrodes from being removed during the process step iv).

2. The method according to claim 1, wherein the process step iv) is a deep reactive-ion etching process step, wherein the structured first protection layer acts as an etching stop to prevent etching of the first and second electrodes during the process step iv).

3. The method according to claim 1, wherein the sensing cavity is partially or completely filled with a sensitive substance, the sensitive substance being chosen such that the sensitive substance has a measurable second parameter, wherein, when the sensitive substance is in contact with the test substance, the second parameter of the sensitive substance varies upon variation of a measurement parameter of the test substance.

4. The method according to claim 1, wherein the substrate is made from a material selected from the group comprising silicon and other semiconductor materials.

5. The method according to claim 1, wherein the first and second electrodes and the sacrificial layer each have an out-of-plane thickness of 50 nanometers to 250 nanometers, or of 160 nanometers to 240 nanometers.

6. The method according to claim 1, wherein the structured first protection layer
   either protrudes in the in-plane direction over the respective first or second electrode in the in-plane direction or is removed after the process step iv).

7. The method according to claim 1, wherein the stack further comprises a second protection layer, the second protection layer covering the first and second electrodes, or the first and second electrodes and the sacrificial layer, the second protection layer having an out-of-plane thickness of
   30 nanometers to 250 nanometers,
   80 nanometers to 120 nanometers, or
   100 nanometers.

8. The method according to claim 7, wherein the process step iv) is carried out such that the first and second electrodes remain covered by the second protection layer such that the first and second electrodes are protected against external influences.

9. The method according to claim 1, wherein the sacrificial layer is completely removed during the process step iv).

10. The method according to claim 1, wherein, after the process step iv), at least a back side of the stack is covered by a third protection layer, the third protection layer having an out-of-plane thickness of 20 nanometers to 350 nanometers, or 120 nanometers to 180 nanometers.

11. The method according to claim 1, wherein said first parameter of the test substance is a humidity of the test substance.

12. The method according to claim 1, wherein the first and second electrodes and the sacrificial layer are made from materials selected from the group consisting of doped polysilicon or any other standard CMOS polysilicon layer materials.

13. The method according to claim 3, wherein the first and second electrodes form a capacitor with the sensitive substance acting as a dielectric in the capacitor.

14. The method according to claim 3, wherein the sensitive substance is a polymer substance and the second parameter is a relative permittivity of that polymer substance, the relative permittivity changing upon absorption or desorption of humidity from the test substance when the sensitive substance is in contact with the test substance.

15. The method according to claim 3, wherein an out-of-plane thickness of the sensitive substance is
   0.5 micrometers to 15 micrometers,
   5.6 micrometers to 8.4 micrometers, or
   7 micrometers.

16. The method according to claim 4, wherein the semiconductor material has an out-of-plane thickness of 100 micrometers to 1000 micrometers, or of 200 micrometers to 500 micrometers.

17. The method according to claim 5, wherein the first and second electrodes are structured in an interdigitated manner with respect to one another;
   wherein the first and second electrodes and the sacrificial layer each have an in-plane width of
      80 nanometers to 1000 nanometers,
      140 nanometers to 260 nanometers, or
      200 nanometers.

18. The method according to claim 5, wherein an in-plane distance between the first or second electrode and the sacrificial layer is at least 150 nanometers, and wherein an in-plane distance between the first electrode and the second electrode is
   150 nanometers to 1000 nanometers,
   400 nanometers to 600 nanometers, or
   500 nanometers.

19. The method according to claim 5,
   wherein the out-of-plane thickness of the passivation layer is
      500 nanometers to 1500 nanometers,
      720 nanometers to 1080 nanometers, or
      900 nanometers, or
   wherein the passivation layer comprises or consists of SiO2.

20. The method according to claim 6,
   wherein the structured first protection layer is a silicon oxide or a silicon nitride layer, or
   wherein an out-of-plane thickness of the structured first protection layer ranges from 100 nanometers to 600 nanometers,
ranges from 320 nanometers to 480 nanometers, or
is 400 nanometers.

21. The method according to claim 6, wherein the first protection layer protrudes in the in-plane direction over the respective first or second electrode by up to 100 nanometers.

22. The method according to claim 7, wherein second protection layer is made from SiN.

23. The method according to claim 10, wherein third protection layer is made from SiN.

* * * * *